United States Patent [19]
Sarfaty et al.

[11] Patent Number: 6,034,781
[45] Date of Patent: Mar. 7, 2000

[54] ELECTRO-OPTICAL PLASMA PROBE

[75] Inventors: Moshe Sarfaty, Santa Clara, Calif.;
Noah Hershkowitz, Madison, Wis.

[73] Assignee: Wisconsin Alumni Research Foundation, Madison, Wis.

[21] Appl. No.: 09/085,079

[22] Filed: May 26, 1998

[51] Int. Cl.[7] .................................................. G01N 21/00
[52] U.S. Cl. ......................................................... 356/436
[58] Field of Search ............................. 356/73, 316, 313, 356/36, 440, 410, 413–414, 417, 432, 436, 445–448; 385/115, 117, 85, 902, 38, 119, 88, 118, 113, 12, 13; 250/288, 458.1, 459.1, 461.1, 461.2, 227.11–227.32; 324/318, 332, 344, 175, 96, 724; 156/345

[56] References Cited

U.S. PATENT DOCUMENTS

| | | |
|---|---|---|
| 3,292,079 | 12/1966 | Schindler . |
| 3,356,885 | 12/1967 | Beck . |
| 4,637,729 | 1/1987 | Schoch . |
| 4,859,277 | 8/1989 | Barna et al. . |
| 5,085,499 | 2/1992 | Griffin et al. . |
| 5,339,039 | 8/1994 | Carlile et al. . |
| 5,359,282 | 10/1994 | Teii et al. . |
| 5,448,173 | 9/1995 | Shinohara et al. . |
| 5,500,076 | 3/1996 | Jerbic . |
| 5,523,955 | 6/1996 | Heckman . |
| 5,570,175 | 10/1996 | Dobele et al. . |
| 5,627,640 | 5/1997 | Chang et al. . |
| 5,652,810 | 7/1997 | Tipton et al. . |
| 5,653,811 | 8/1997 | Chan . |

OTHER PUBLICATIONS

G. Fiksel, et al., An Optical Probe For Local Measurements of Fast Plasma Ion Dynamics, Review of Scientific Instruments, vol. 69, No. 5, May, 1998, pp. 2024–2026.

*Primary Examiner*—K. P. Hantis
*Attorney, Agent, or Firm*—Foley & Lardner

[57] ABSTRACT

A plasma probe enables simultaneous localized electrostatic measurements and optical emission spectroscopy. The probe has a support arm with an elongated longitudinally extending section and a bend section at the end of which is supported an electrical probe element composed of back-to-back charge collection plates separated by an insulating spacer. The inner plate faces an opening in the end of the elongated support arm section which defines a collimating channel. An optical fiber extends through the support arm and has an aperture in the collimating channel to receive light emitted from the plasma between the end of the elongated section of the support arm and the inner charge collection plate. The electrical probe element acts as a blocking element to block light emitted from the plasma outside of the region between the electrical probe element and the end of the support arm section. Electrical wires extend through the probe from the charge collection plates to charge detectors, allowing measurements of electron density, Electron Energy Distribution Function and ion flow. The light received by the optical fiber is detected by a spectrometer to carry out Optical Emission Spectroscopy, which can be correlated with the information obtained from the charge collection plates. The probe can be moved around a plasma confinement chamber to provide spatially localized measurements of plasma characteristics at various positions within the chamber.

18 Claims, 9 Drawing Sheets

ELECTRO-OPTICAL PLASMA PROBE

This invention was made with United States government support awarded by the following agencies: DOE Grant No. DE-FG02-88ER53264 and NSF Grant No. EEC-8721545, ECS-9529565. The United States has certain rights in this invention.

FIELD OF THE INVENTION

This invention pertains generally to methods and apparatus for the spatially resolved measurement of plasma characteristics such as plasma density, Electron Energy Distribution Function, potentials, ion velocity, and electromagnetic fields, and to spatially resolved actinometry.

BACKGROUND OF THE INVENTION

A major concern in the plasma processing of materials is the spatial uniformity of the process. Process uniformity depends strongly on the spatial distribution of both charged and neutral particle densities and velocities as well as potentials. Process uniformity is a key requirement to enable large semiconductor wafers or flat panels to be processed by plasma.

Electrical probes have long been used with plasmas to measure electron density, Electron Energy Distribution Function (EEDF), potentials, and electromagnetic fields. See, e.g., F. F. Chen, in *Plasma Diagnostic Techniques*, edited by R. H. Huddlestone and S. L. Leonard, Academic Press, New York, 1965, pp. 113–200, and L. Schott, in *Plasma Diagnostics*, edited by W. Lochte-Holtgreven, North-Holland Publishers, Amsterdam, 1968, pp. 668–731. Mach probes are electrical probes that have the capability of measuring ion flow velocities. See, e.g., I. H. Hutchinson, *Principles of Plasma Diagnostics*, Cambridge University Press, New York, 1987.

Optical Emission Spectroscopy (OES) has been extensively used in plasma processing to obtain optical emission information that is integrated along the line-of-sight. To obtain spatial resolution, Abel inversion of a multi-direction OES is most frequently used, assuming cylindrical symmetry of the plasma. In conventional actinometry, a known quantity of an inert gas is added to the reactive gas and the distribution of radicals is obtained by analyzing the ratio of light emitted from the radicals and the reference gas, with argon typically being used with fluorine and xenon with chlorine. The excitation rate ratio between the reference gas and the radical species depends strongly on the local EEDF. In conventional actinometry, the emitted light is received from a volume which typically extends across the chamber containing the plasma so that the measurements of the emitted light that are obtained provide only the average emission over the entire volume within the chamber. This limits the accuracy of the actinometry measurements since the EEDF is typically not uniform through the whole volume over which the light emissions are detected.

SUMMARY OF THE INVENTION

A plasma probe in accordance with the present invention provides simultaneous localized electrostatic measurements and optical emission spectroscopy. The probe is well suited to correlating the optical emission spectroscopy measurements over a spatially constrained volume with a Mach probe measurement of electron density, Electron Energy Distribution Function and ion flow. The probe is minimally disruptive of the plasma into which it is inserted, allowing high precision measurements of the spatial uniformity of plasmas such as those used in semiconductor processing.

The probe in accordance with the invention has an elongated longitudinally extending support arm with a distal end adapted to be inserted into the plasma and moved about the chamber containing the plasma. An optical fiber is carried by the support arm and has an aperture for collection of light which is preferably collimated by a collimator. A light blocking element is mounted to the support arm at a position spaced longitudinally from the aperture of the optical fiber so that the fiber collects light only from the axial region between the terminus of the fiber and the blocking element and not from the regions beyond the blocking element, ensuring a spatially limited integration length for the plasma emission light collected by the optical fiber.

In the preferred implementation of the invention, the blocking element is an electrical probe element comprising a Mach probe formed of two electrically conducting charge collection plates mounted on and separated by an electrically insulating spacer. Electrical wires are connected to the plates and carried by the support arm to a position remote from the probe end where they can be connected to detection equipment. Similarly, the optical fiber extends to a remote location where it can be coupled to a spectrometer and detector. The electrical charge collection plates comprising the electrical probe element are preferably mounted such that a face of one of the plates is perpendicular to the axial direction and faces the aperture of the optical fiber. A U-shaped bend section of the support arm preferably joins an elongated section of the support arm at the terminal end of the optical fiber, with a first leg of the bend extending radially away from the axis of the elongated arm section, and with a longitudinally extending section positioned substantially away from the line of sight of the optical fiber (and from the electrical probe element) to minimize interference with the plasma in the region between the optical fiber aperture and the charge collection plates of the electrical probe element. A further inwardly radially extending leg of the bend section supports the electrically conducting plates. Preferably, the electrical wires and the optical fiber extend through a hollow bore or bores within the elongated arm section so as to be physically and electrically isolated thereby from the surrounding plasma.

The aperture end of the optical fiber is preferably recessed within a collimating channel in the support arm to partially protect the end of the fiber from damage or coating by the plasma. The collimating channel limits the optical acceptance angle of the emission light reaching the aperture of the fiber, preferably so that the field of view of the aperture of the fiber is no greater than the area of the facing charge collection plate, which may be formed as a circular disk. In this manner, the spatial resolution in both radial and longitudinal directions of the emitted light gathered by the optical fiber is closely controlled.

The charge collected by the two oppositely facing plates may be measured, and the ratio of the ion saturation currents of the two counterfacing charge collectors determined, to provide an indication of the ion flow velocity perpendicular to the surfaces of the plates.

The probe may be utilized to obtain a correlation of the plasma properties as measured by the electrical charge collection plates and with localized actinometry utilizing light gathered by the optical fiber as the electro-optical probe is moved across the plasma volume in a confinement chamber, allowing mapping of the plasma characteristics within the plasma volume.

Further objects, features and advantages of the invention will be apparent from the following detailed description when taken in conjunction with the accompanying drawings.

DETAILED DESCRIPTION OF THE INVENTION

Figure 1:
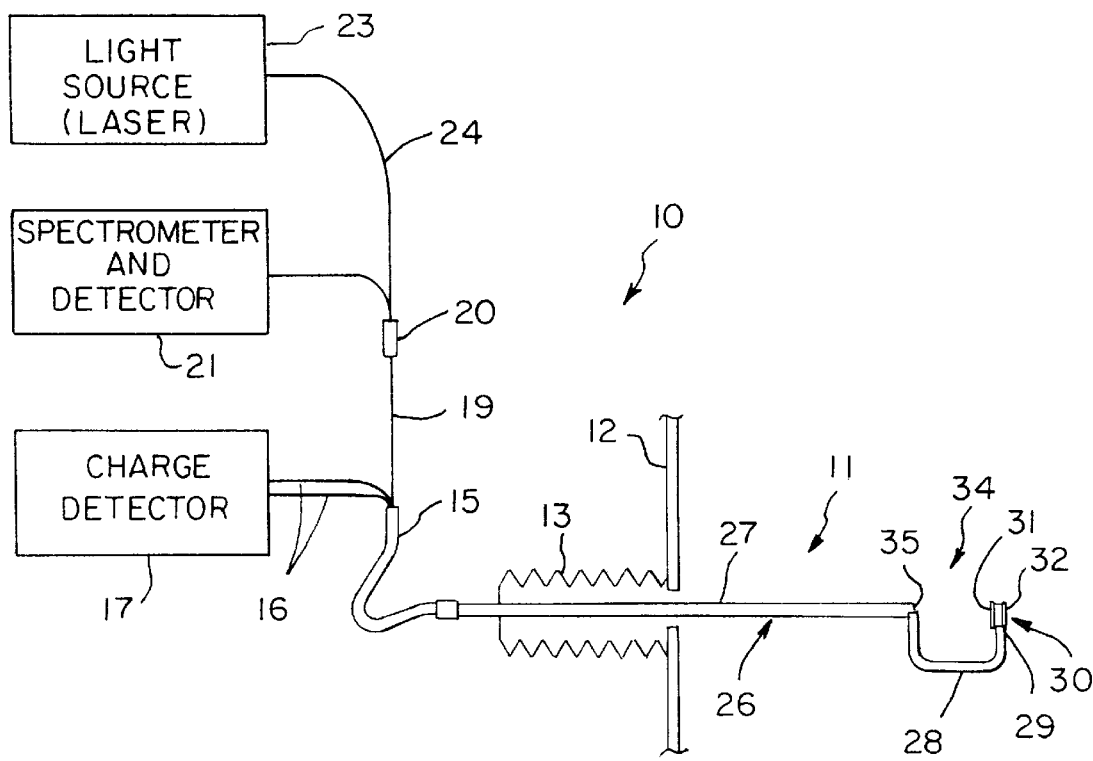
FIG. 1 is a simplified view of a plasma characterization system incorporating the electro-optical probe of the invention.

A plasma measurement system is shown generally at in FIG. 1 incorporating an electro-optical probe 11 in accordance with the invention. The probe 11 is mounted to pass through a wall 12 of a plasma confinement vessel, and may be secured to the wall 12 with a bellows 13 or other conventional mechanism to allow the probe 11 to be advanced and retracted and manipulated in the interior of the plasma containment vessel. Extending from the probe 11 is a cable 15 from which extend electrical wires 16 which are connected to an electrical charge detector 17. An optical fiber 19 also extends from the cable 15 through an optional fiber optic directional coupler 20 to a spectrometer and detector 21. The fiber optic directional coupler 20 may be utilized with a light source such as a laser 23 which provides excitation light on an optical fiber 24 to the coupler 20, to transmit the laser light through the optical fiber 19 to the probe 11 within the plasma chamber, as discussed further below.

Figure 2:
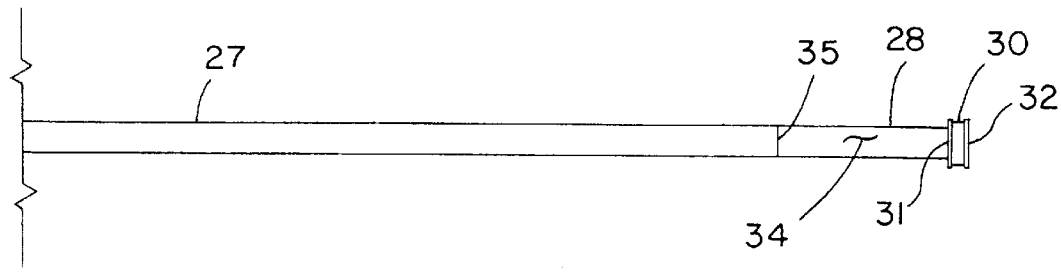
FIG. 2 is a top view of the electro-optical probe of the invention.

As generally illustrated in FIG. 1, the electro-optical probe 11 has a support arm 26 that includes a straight, elongated, longitudinally extending section 27, and a bend section 28. At the distal end 29 of the arm 26 is mounted an electrical probe and blocking element 30 comprising back-to-back electrically conducting charge collection plates 31 and 32. An unobstructed volume 34 is defined between a terminus 35 of the longitudinally extending section 27 of the support arm and the inwardly facing conductive plate 31. As illustrated in FIG. 1 and the top view of the probe in FIG. 2, the plates 31 and 32, which may be circular disks, are perpendicular to the axial direction defined along the longitudinally extending section 27 of the support arm. The end of the optical fiber 19 (not shown in FIGS. 1 and 2) is positioned at the terminus 35 of the longitudinal arm 27 or, preferably, recessed inwardly from the terminus 35.

Figure 3:
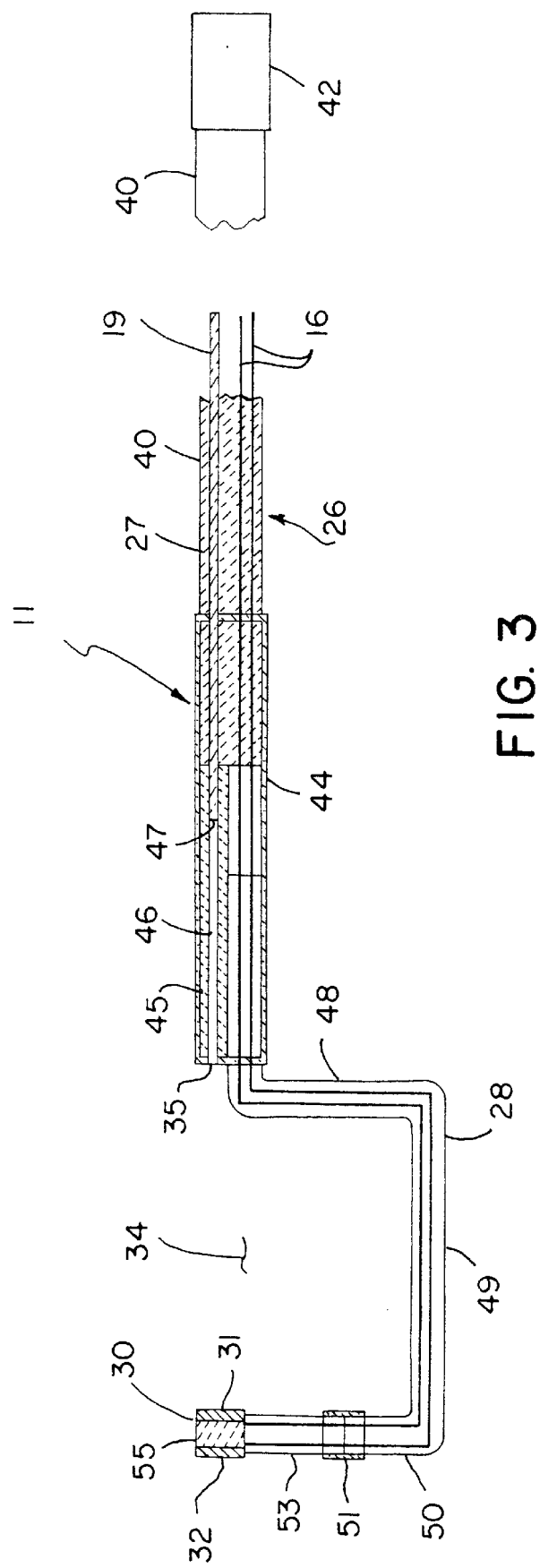
FIG. 3 is a cross-sectional view in greater detail of the electro-optical probe of the invention.

A cross-sectional view of a preferred construction for the electro-optical probe 11 is shown in FIG. 3. The straight, longitudinally extending section 27 of the support arm 26 may include a straight section of ceramic tubing 40 (e.g., 5 mm outside diameter) having a hollow bore which, e.g., may be divided into four lumens, through which extend the optical fiber 19 (e.g., quartz fiber optic, 1 mm diameter), and the electrical wires 16. The proximal end section of the support arm 26 may have a stainless steel tube 42 (6.5 mm outside diameter) enclosing the ceramic tube 40. A tube 44 (e.g., Pyrex™, 7 mm outside diameter) preferably is mounted at the outermost end of the support arm section 27 to enclose a portion of the ceramic tube 40, and a collimator section 45 formed as, e.g., a ceramic tube with an interior channel 46 (e.g., 1.5 mm inside diameter). The optical fiber 19 extends into the channel 46 of the collimator 45, with the end aperture 47 of the fiber 19 spaced well inwardly (e.g., 2.54 cm) from the opening of the channel 46 at the end 35 of the longitudinal section of the support arm for protection of the end 47 of the fiber from the surrounding plasma and for collimation of the emission light that is received through the channel 46 by the aperture end 47 of the optical fiber. By recessing the end 47 of the fiber a sufficient distance into the channel 46, deposition on the fiber end is reduced sufficiently that localized actinometry may be carried our in deposition plasmas.

The bend section 28 of the support arm preferably is U-shaped as shown, and may be formed of a one-piece glass tube (e.g., Pyrex™ 3 mm outside diameter) having a radially extending segment 48, then a straight segment 49 extending longitudinally from the radial segment 48, and then an inwardly radially extending segment 50 on which the electrical probe element 30 is mounted. A coupling 51 (e.g., Pyrex™) couples the section 50 of the bend to a ceramic tube 53 (e.g., 2 mm outside diameter). The charge collection plates 31 and 32 are formed, for example, of 3.175 mm diameter tantalum disks 0.127 mm thick. The disks 31 and 32 are secured to and separated from each other by an insulating spacer element 55, preferably a ceramic casting material (e.g., 1.5 mm thick). The wires 16 (e.g., 32 gauge Teflon™ coated wires) extend to and are electrically connected to the inward side of the metal disks 31 and 32 (the side adjacent to the spacer element 55) and are preferably protected thereby from the surrounding plasma.

Exemplary dimensions for the probe shown in FIG. 3 are 26 cm from the end of the tube 42 to the outwardmost plate 32, 2.54 cm from the end 35 of the support arm section 37 to the plate 32, 3 cm from the bottom of the straight section 49 of the bend to the top of the disks 31 and 32, and 2.54 cm length of the collimating channel 46 from the end 35 to the aperture end 47 of the optical fiber.

The collimator channel 46 limits the field of view of the aperture 47 of the optical fiber, preferably limiting it to the extent of the face of the electrical charge collector plate 31, which effectively acts as a blocking element to prevent light emitted from any region other than the space 34 from reaching the aperture end of the optical fiber. The face of the tantalum disk 31 may be treated or coated to minimize reflections from the face of light emitted from other locations into the collimating channel 46.

Utilizing the probe of the present invention, light collected by the optical fiber may be measured by a spectrometer and detector 21 comprising an optical-multi-channel analyzer placed at the output slit of a spectrometer to provide line emission intensities that are used to obtain density profiles of neutral radicals. With appropriate spectral resolution, the spatial distribution of other observable characteristics of the plasma, such as particle thermal and directed velocity (Doppler width and shift), magnetic fields (Zeeman splitting) electric fields (Stark broadening and shift), can be obtained from the line emission profile.

Because the collected line emission data from the optical fiber are induced by the plasma electrons, knowledge of the local EEDF measured by the probe is essential for correct interpretation of the optical emission spectroscopy signals as particle concentration. The excitation rate ratio between the reference trace gas (e.g., argon/xenon) and the radical species (fluorine/chlorine) depends strongly on the details of the local EEDF. The dependence of the electron excitation rate ratios on the electron energy is important to the actinometry method of invention to determine radical density.

The back-to-back tantalum disks 31 and 32 serve as charge collectors to measure the local electrical properties of the plasma. The inner disk 31 was spaced 24 mm from the end 35 of the straight section of the support arm. The collimator formed by the channel 46 limits the fiber acceptance angle, e.g., to less than 1.5°. The collimation of the light reaching the optical fiber at its aperture end 47 limits the field of view to less than the diameter of the disk 31, so that the optical emissions are collected from a column effectively about 24 mm long and 2 mm wide. The light collection volume can be adjusted by movement of the fiber inside the collimating channel 46 either toward or away from the terminating end 35.

The bend section 28 minimizes the perturbations of the plasma in the region between the end 35 and the inner disk 31 that might otherwise be caused by the support arm structure adjacent to that region. With the exemplary spacings given above, the perturbation of the plasma is minimal and does not substantially affect the accuracy of the measurements. The grounded stainless steel tube 42 preferably is used to cover the ceramic tube to reduce the radio frequency noise in the electrical signals on the wires 16. The induced RF noise may be further reduced from the current-voltage (I-V) measurements obtained from the signal wires 16 by using low-pass and band rejection filters. The coupling of scattered light to the optical fiber is negligible relative to the light collection from the spatially constrained volume 34.

Exemplary optical emission signals were acquired by the unit 21 having a 30 cm spectrometer with a grating of 1200 grooves/mm. A water-cooled nitrogen-purged optical multichannel analyzer was used to record light signals at the output slit of the spectrometer. A spectral resolution of about 0.06 nm/pixel is obtained in the spectral range of 700–850 nm. Gas mass spectrometry data well obtained by a Residual Gas Analyzer (RGA), which was calibrated before and after the experiments by flowing argon and xenon gases in accordance with the experimental runs. The calibration provides a relation between the RGA and the ionization-gauge pressure readouts, i.e., absolute number density or pressure for the RGA readouts for the noble gases. The density of chlorine or fluorine radicals are determined by introducing into the discharge 4% of xenon or argon gas, respectively. The measurements described below were made at an axial distance of about 1 cm above a silicon wafer. The radial scans were taken in random order across an entire plasma confinement chamber. The spatially resolved radical densities are compared with line-of-sight optical emission spectrometry data collected from a cylindrical plasma volume of about 1 cm diameter centered about 1 cm above the wafer. The line integrated measurements are done through a side window using a lens to collimate the fiber light collection.

Figure 4:
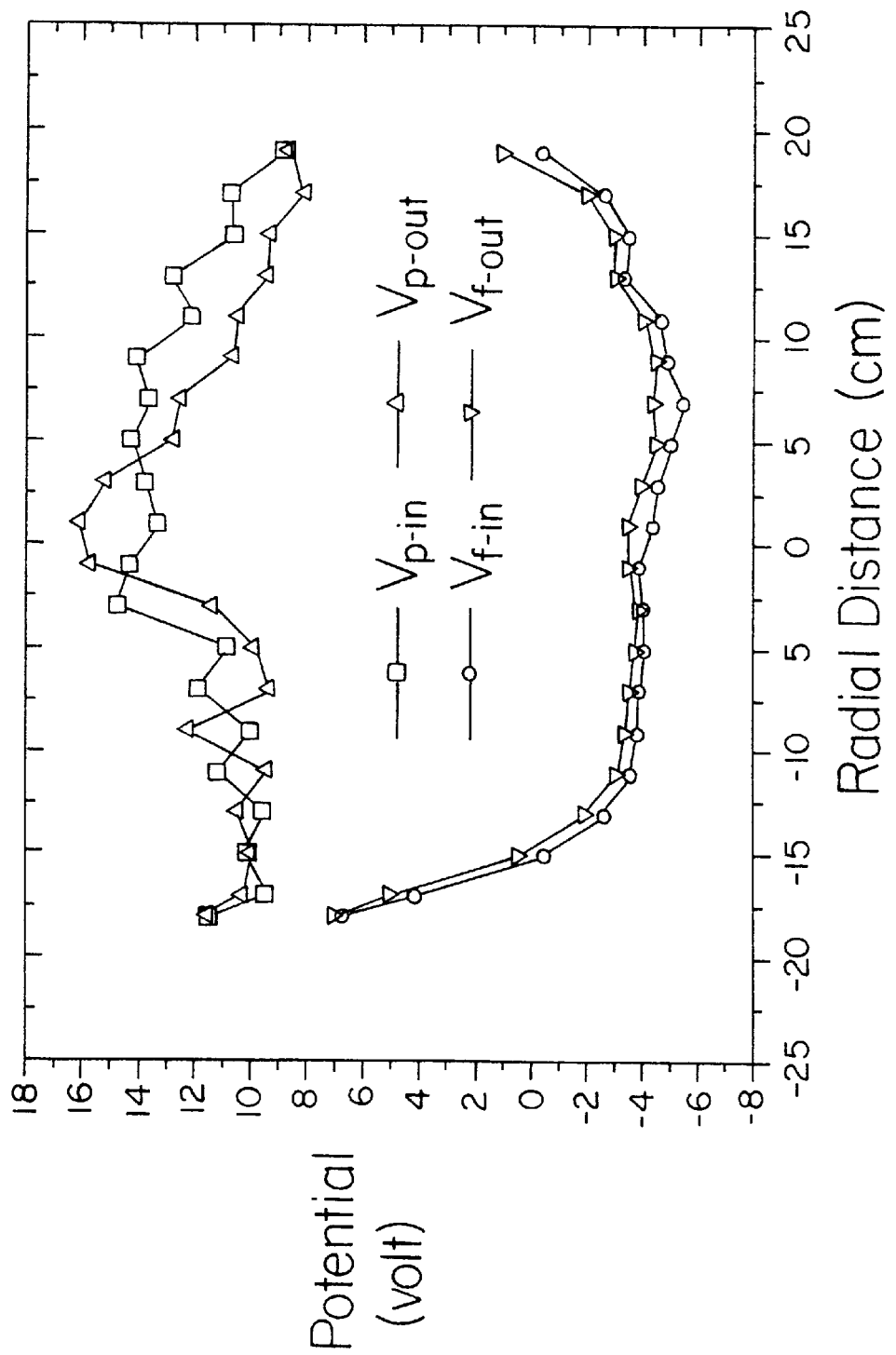
FIG. 4 are graphs of experimental data illustrating radial potential variations in chlorine plasma as measured utilizing the probe of the invention.

The spatial distribution of the plasma ($V_p$) and floating ($V_f$) potentials are determined by both the inner 31 and outer 32 disk charge collector plate of the probe 11. The radial potential variations in chlorine plasma, shown in FIG. 4, is measured at a distance of 1 cm above the wafer. The floating potential is obtained from the zero crossing of the I-V trace, while the plasma potential is determined from the zero crossing of its second derivative. The plasma potential decreases towards the walls while the floating potential increases. As seen in FIG. 4, the similar potentials obtained by both of the charge collectors 31 and 32 indicate similar plasma conditions in the open plasma and the resolved plasma volume 34.

Figure 5:
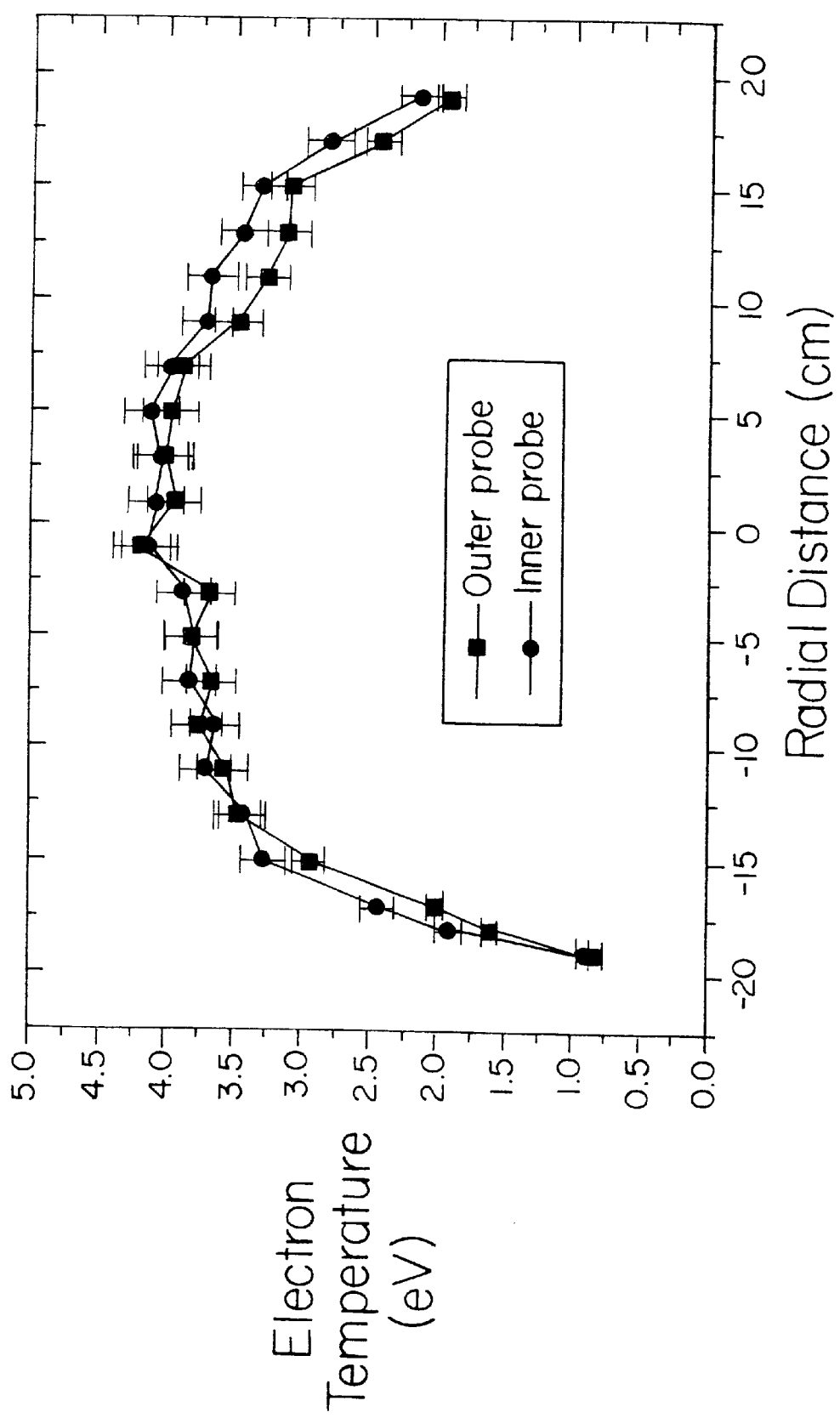
FIG. 5 are graphs illustrating the radial dependence of the electron temperature obtained utilizing the electro-optical probe of the invention.

The electron temperature was evaluated both by fitting a Maxwellian energy distribution function to the second derivative of the I-V curve and by fitting an exponential function to the electron I-V trace in the voltage range below the plasma potential, i.e., the electron retarding part. The radial dependence of the electron temperature, shown in FIG. 5, is obtained by the former method. The highest electron temperature is measured at the center of the chamber with a small decreasing gradient towards 15 cm from the center. A steeper gradient is observed beyond 15 cm radius, at a distance of 5 cm from the chamber wall. This distance is close to the outer edge of the rf antenna. An almost constant relation is observed between the sheath potential $V_s = V_p - V_f$ and the electron temperature of $V_s/T_e \sim 4.5$ across the chamber diameter. The inner and outer charge collector traces yield similar electron temperature profile within the experimental error. A slightly higher temperature is obtained by the inner collector at radial distances larger than 15 cm.

Figure 6:
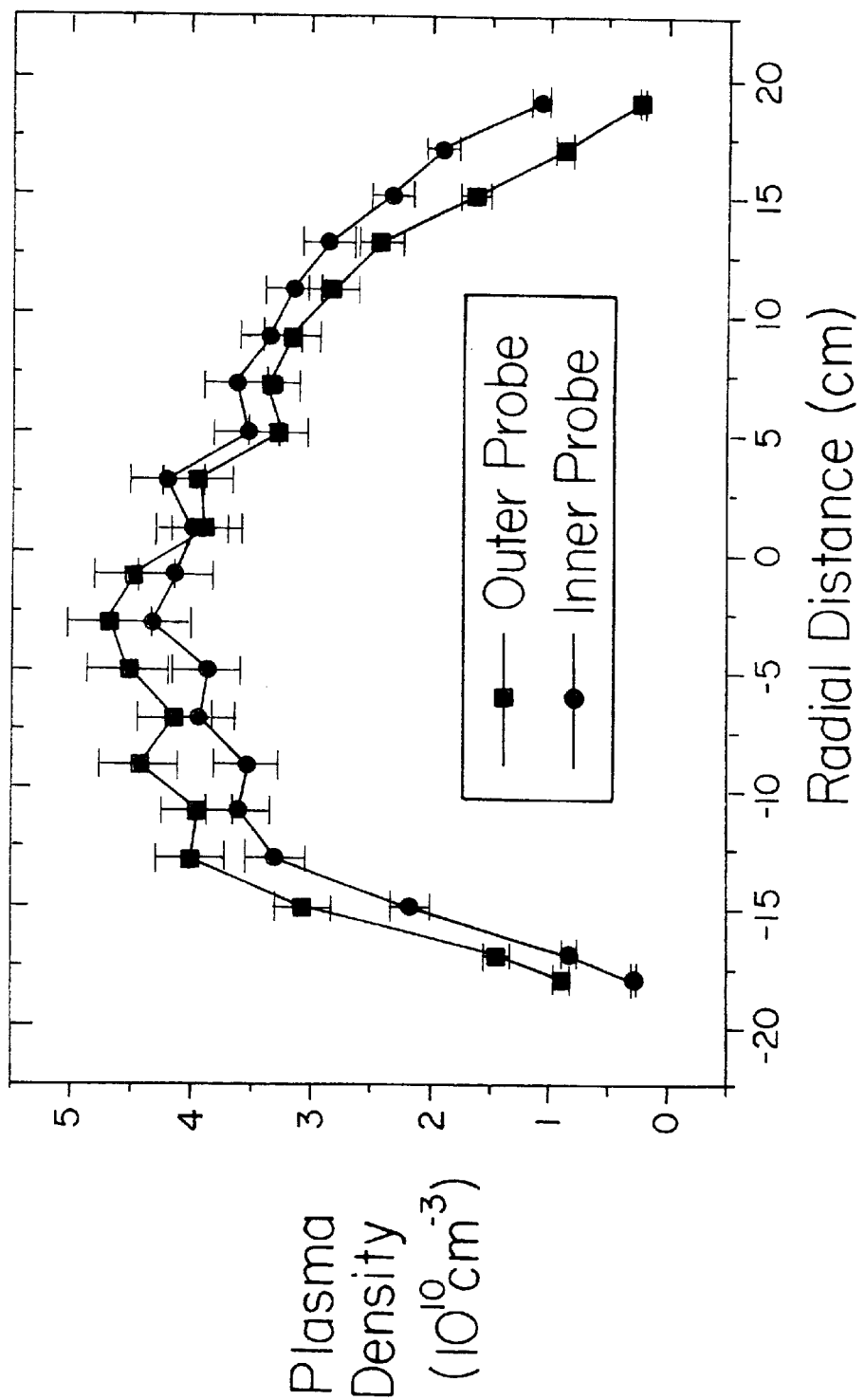
FIG. 6 are graphs of the radial profile of the electron density obtained from the integration of the second derivative of the I-V curve obtained utilizing the electro-optical probe of the invention.

The radial profile of the electron density, shown in FIG. 6, is obtained from the integration of the second derivative of the I-V curve at each point. The radical profile of the plasma density shows small density gradients in the center of the chamber and an increasing gradient close to the chamber walls. It is important to note that the radial density profiles obtained by the two charge collectors (31 and 32) cross each other around the chamber center. The density determined by the collector plate 31 and 32 that faces the nearest chamber wall is typically lower than that determined by the opposite collector. A similar behavior is also observed in the ion saturation current measured by the two charge collectors 31 and 32. This difference is attributed to the radial component of the ion flow. A lower density is measured by the collector that is in the shadow of the radial flow.

Figure 7:
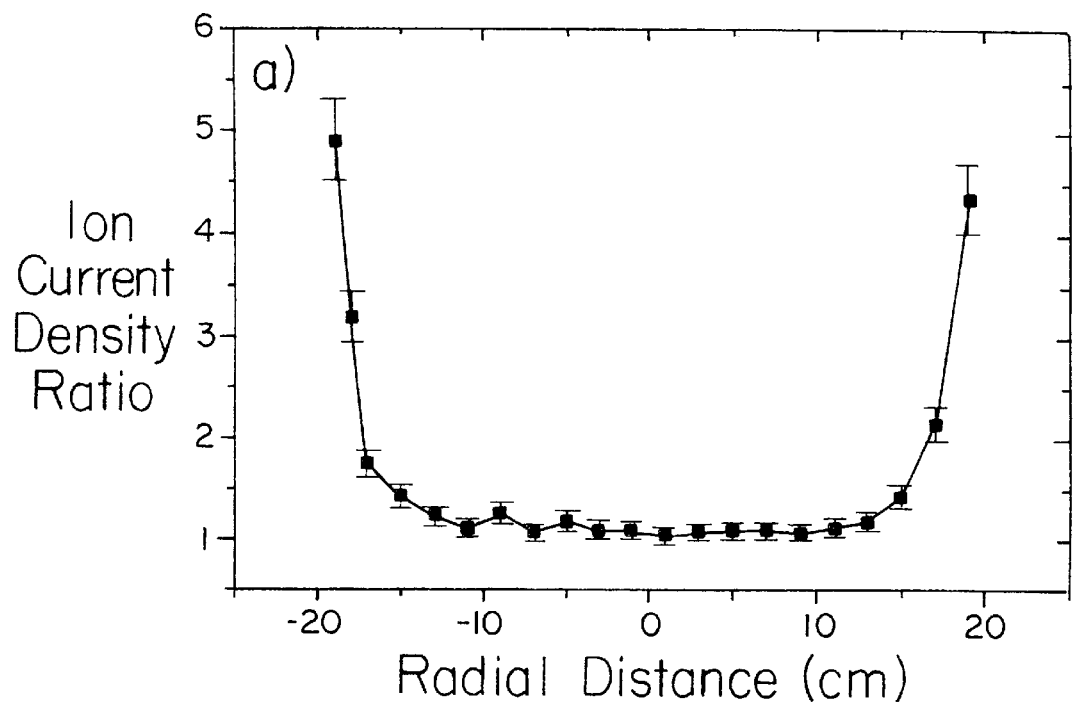
FIG. 7 are graphs of the radial profile of the ion current density ratio obtained utilizing the electro-optical probe of the invention.
Figure 8:
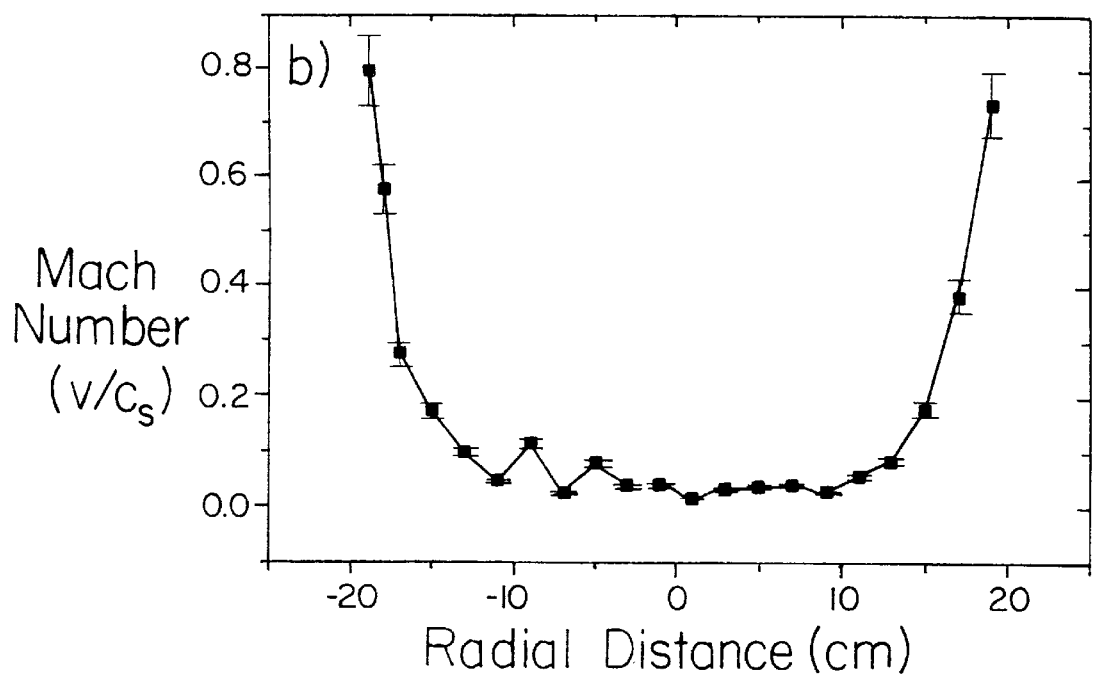
FIG. 8 are graphs of the radial profile of the ion Mach number obtained utilizing the electro-optical probe.

The ion current density ratio of the two collectors can be used to determine the component of the ion flow velocity perpendicular to the disk surface, which is radial in this case. Similarly, if the probe is introduced along the axial direction, the axial component can be determined. The radial ion current density ratio, shown in FIG. 7, indicates a larger radial ion flow close to the chamber walls. The ion Mach number, $M = V_i/C_s$, or ion velocity, $V_i$, normalized to the ion sound speed, $C_s=(T_e/M_i)^{1/2}$, shown in FIG. 8, is calculated from the ion current density ratios assuming a pure singly ionized C1 plasma. The relation between the ion current density ratio, R, and the ion Mach number is given by $R=\exp(2M)$, derived from the Mach probe theory. The radial profile of the measured electron temperature, shown in FIG. 5, is required to transform the ion Mach number to radial ion velocities. In spite of the about 4-fold drop in the electron temperature near the walls, the radial ion velocities increase as the plasma approaches the chamber walls. The measured radial component of the ion velocities reflects the radial gradients of the plasma density profile, shown in FIG. 6, and is indicative of the plasma presheath near the chamber walls. To better evaluate the ion radial velocity, Doppler shift optical emission spectroscopy or laser induced fluorescence of the main plasma ion may be measured and compared with the Mach relation used above.

The optical part of the probe collects line emission induced by the plasma from a resolved volume, restricted by the disk collector 31 and the optical fiber acceptance angle, which is collimated by the ceramic tube 45 it is recessed in. A technique known as actinometry may be used in accordance with the invention to determine the concentration of reactive species such as fluorine and chlorine. Actinometry uses the emission of a non-reactive noble gas, added in trace amounts to the discharge, to determine the density of a relevant species from its emission intensity. The underlying assumption is that the emission of both the actinometer and the target particle are produced by electron impact excitation from the ground state species. Therefore, the electron-impact cross-sections of both species need to have similar threshold energy and shape as a function of the electron energy. Also, the excited states of both species must decay primarily by photon emission. The inert actinometer gases used here are argon and xenon for fluorine and chlorine density measurements, respectively. To obtain absolute number densities, the amount of the trace gas was measured with a pressure calibrated RGA set at one of the chamber ports. The radial uniformity of the actinometer was confirmed by measuring the local density of the actinometer with a 100 cm long quartz tube of 0.9 cm diameter that was scanned across the chamber diameter. A uniform distribution was observed across the chamber for an operating pressure of 4 mTorr both prior and during the plasma discharge. The spatial distribution of the actinometer is important when the local density of the target radical needs to be determined.

The emission intensity of species x, $I_x$, is given by $$I_x = C_d(\lambda) n_{gx} n_e K_x Q_x b \lambda x \tag{1}$$

where $C_d(\lambda)$ is the detector spectral response, $n_{gx}$ is the ground state density of species x, $n_e$ the electron density, $K_x$ is the electron excitation rate from the ground state to the observed level, $Q_x$ is the quantum yield for photon emission, which is unity at process pressure of 4 mTorr, and $b_{\lambda x}$ is the emission branching ratio for the transitions used. Relating the emission intensities of the target radical to that of the actinometer yields the following expression for the radical ground state population.

The ratio of branching ratios in the last term is available from atomic transition tables and the wavelength response of the detector within the spectral range of 700–830 nm is relatively constant. The number density of the actinometer $$n_{gx} = n_{act} \frac{I_x}{I_{act}} \times \frac{K_{act}(T_e)}{K_x(T_e)} \times \frac{C_{act} b_{\lambda act}}{C_x b_{\lambda x}} \tag{2}$$

was measured with an on-line calibrated RGA stable to within 1% during data acquisition. The line intensities were measured at various positions selected in random order across the chamber diameter. Line intensities measured repeatedly at the center of the chamber during the radial scans show repeatability of about 3%. The electron impact excitation cross-sections, $\sigma_x$, from the ground-state to the energy level observed are taken from experimentally available sources for xenon and argon and computed for argon, fluorine and chlorine. The excitation rate for a Maxwellian EEDF from the ground state to the observed level, $E_{thx}$, are calculated using Eq. 3 below.

$$K_x = \frac{1}{m\pi^{1/2}} \left(\frac{2}{T_e}\right)^{3/2} \int_{E_{thx}}^{\infty} \sigma_x(\varepsilon) \varepsilon e^{-\varepsilon/T_e} d\varepsilon \tag{3}$$

Figure 9:
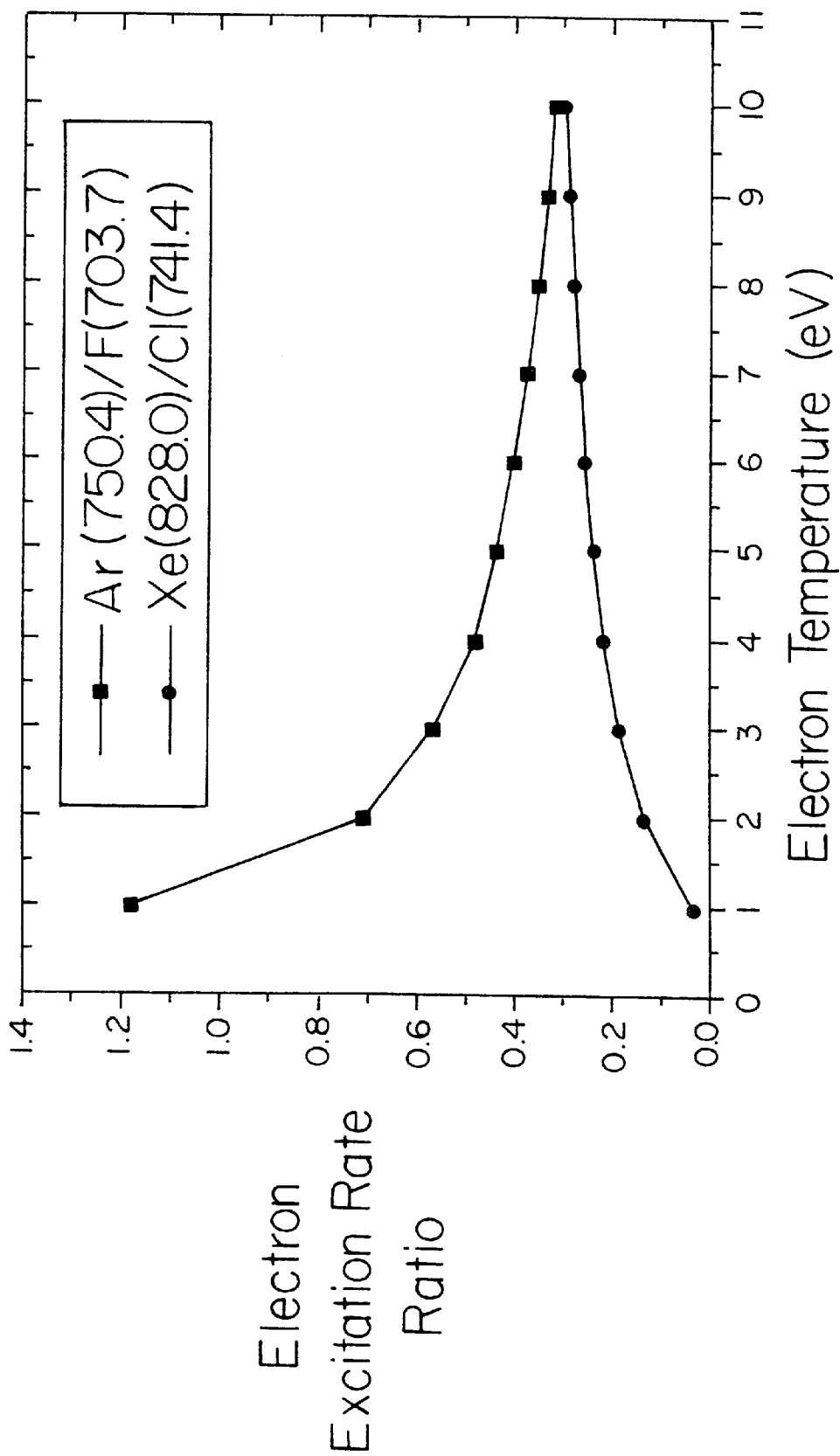
FIG. 9 are graphs illustrating electronic excitation rate ratios a function of electron temperature for argon to fluorine and xenon to chlorine.

The ratios of excitation rates as a function of electron temperature are shown in FIG. 9 both for argon ($1S_2$-$2P_1$ 750.4 nm) to fluorine ($3s[3/2]^2P$-$3p[3/2]^2P$ 703.7 nm) and xenon ($1S_4$-$2P_5$ 828.0 nm) to chlorine ($4s[5/2]^2P$-$4p[3/2]^4P$ 741.4 nm). The spectral lines selected are those whose upper level populations are the least affected by metastable levels. The temperature dependence of these ratios is very important when the number density of the relevant radical needs to be determined using Eq. 2. The radial profile of the electron temperature, determined by fitting a Maxwellian to the measured EEDF, is used here to calculate the radial dependence of the excitation rate ratios. It is important to note that for a case of non-Maxwellian EEDF the measured EEDF can be used in Eq. 3 to calculate the excitation rates.

Figure 10:
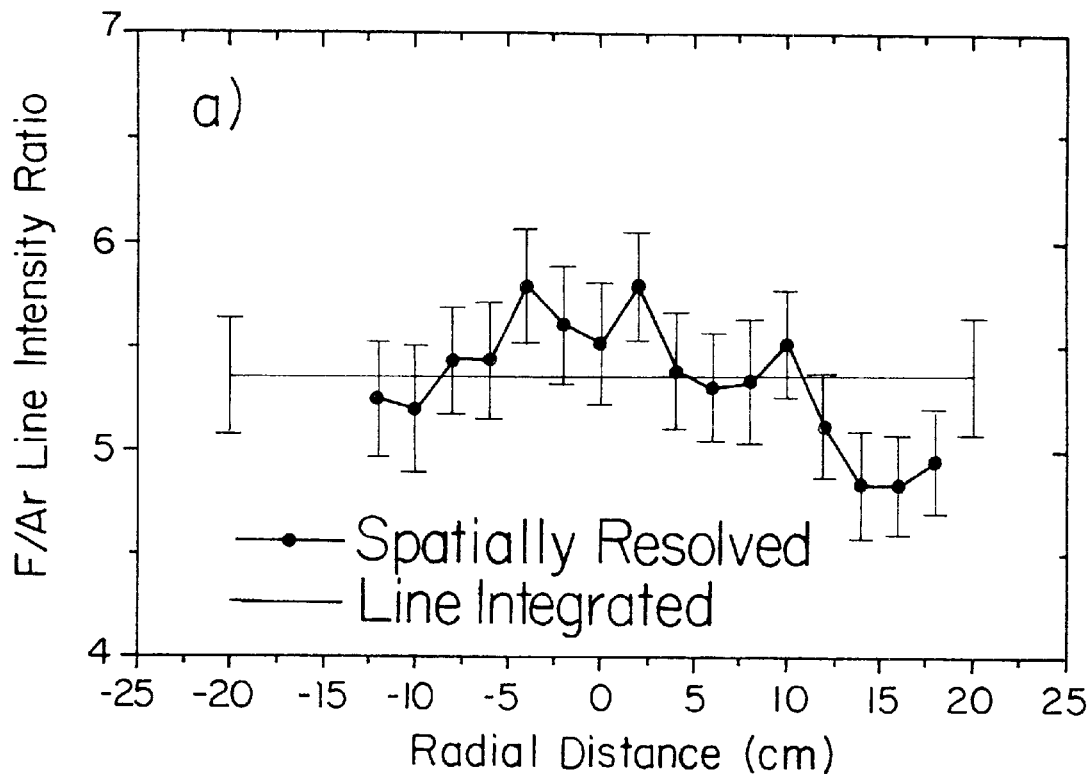
FIG. 10 are graphs illustrating the measured fluorine to argon line intensity ratio as a function of radial distance obtained utilizing the electro-optical probe.
Figure 11:
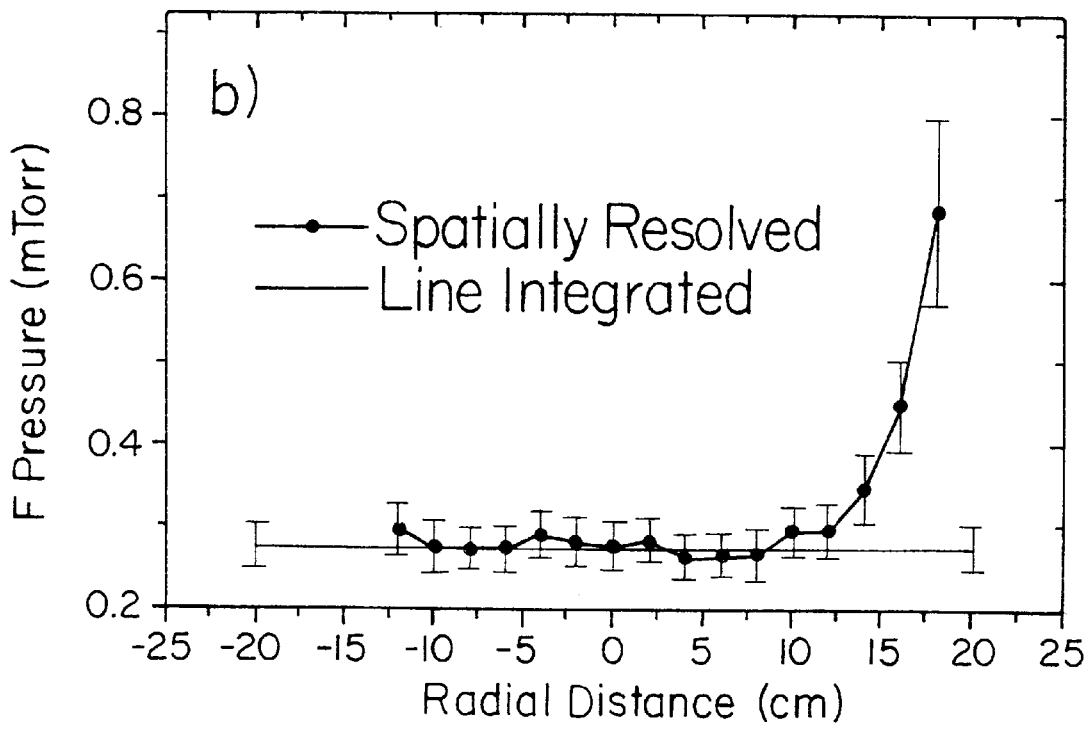
FIG. 11 are graphs of the radial profile of the partial pressure of atomic fluorine in the discharge.

The radially resolved and the line integrated emission intensity ratios of fluorine to argon are given in FIG. 10. The radial profile of the partial pressure of atomic fluorine in the discharge, determined by Eq. 3, is shown in FIG. 11. A clear rise in atomic fluorine partial pressure is observed near the chamber walls. A possible explanation is that ions impinging on the chamber walls which are coated with fluorine containing films can introduce atomic fluorine into the plasma. The line integrated emission intensity ratio measured through a side window agrees with the radially resolved ratios in the bulk of the plasma. The absolute partial pressure of atomic fluorine is determined from the argon partial pressure measured during the scans with the calibrated RGA.

Figure 12:
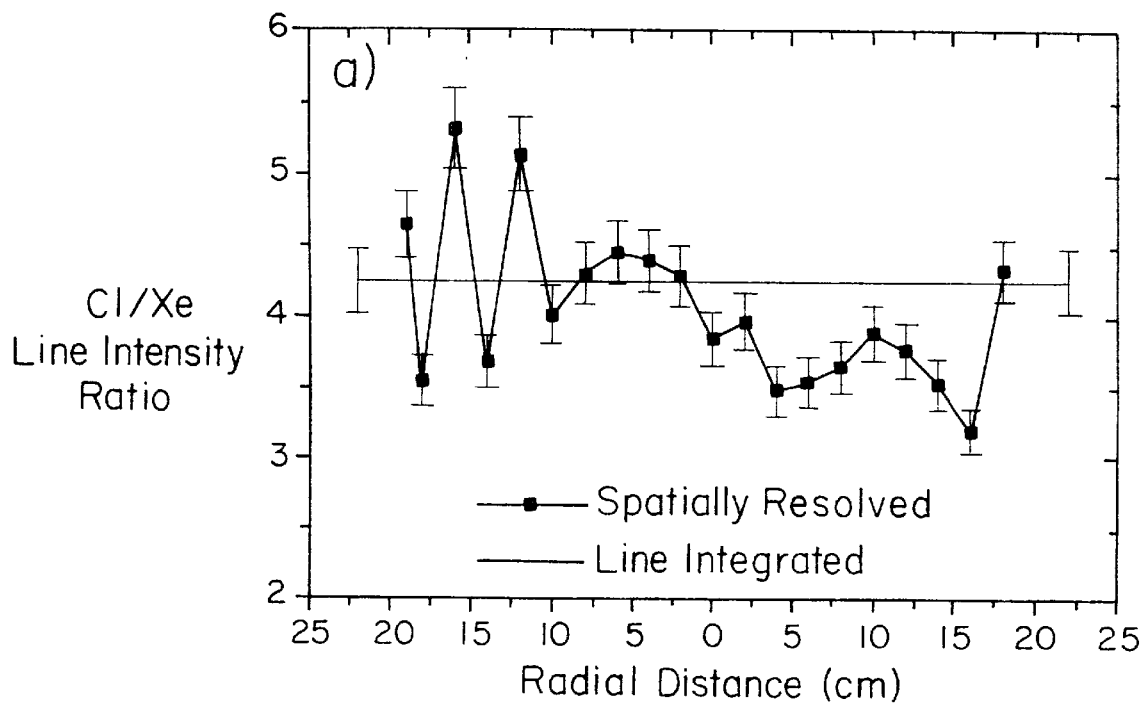
FIG. 12 are graphs of the chlorine to xenon line intensity ratio as a function of radial distance.
Figure 13:
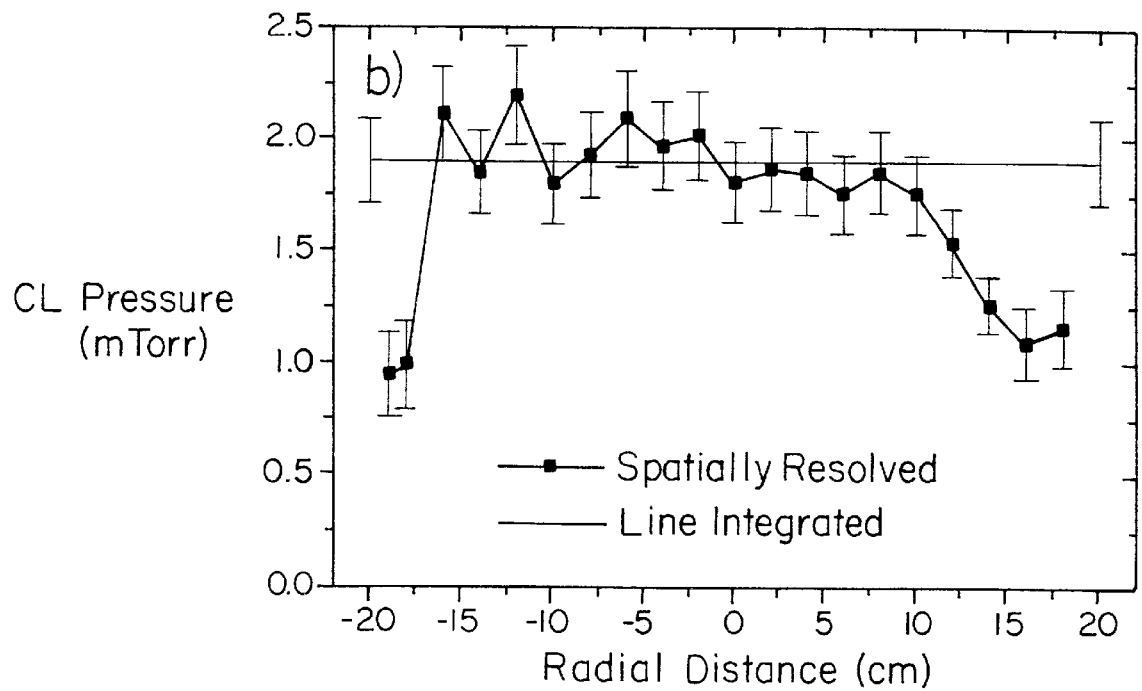
FIG. 13 are graphs of the radial profile of the chlorine partial pressure.

The line intensity ratios of chlorine to xenon as a function of radial position are shown in FIG. 12. The absolute partial pressure profile of chlorine atoms, shown in FIG. 13, is obtained by Eq. 3, after correcting for the radial variations of the excitation rate ratios as a function of the measured electron temperature profile. The partial pressure of atomic chlorine is lower near the chamber walls than in the bulk of the plasma, due to wall recombination of atomic chlorine into molecular chlorine. The ratio of the line integrated emission intensity agrees with the radially resolved ratios measured in the bulk of the plasma.

In the example above, the optical emission spectra collected by the optical fiber is induced by the plasma electrons. optionally, light from the source 23 may be directed by the optical fiber 19 to the spatially resolved plasma volume 34 to induce light emission of various plasma species, and the fluorescence collected by the same optical fiber can be used for diagnostics in the manner discussed above.

Although the support arm section 27 is preferably straight and the distal end 29 of the probe is preferable aligned with the axis of the longitudinally extending support arm section 27, it is understood that the distal end 29 at which the element 30 is mounted may be positioned off-axis or even positioned axially inwardly of the aperture of the optically fiber 19 by appropriate shaping and/or rearrangement of the support arm section 27 and 28.

It is understood that the invention is not confined to the particular embodiments set forth herein as illustrative, but embraces all such modified forms thereof as come within the scope of the following claims.

What is claimed is:

1. A probe for plasma measurements comprising:

(a) a probe support arm with a distal end;

(b) an optical fiber carried by the support arm and having an aperture for the collection of light by the fiber;

(c) a light blocking element mounted to the distal end of the support arm at a position spaced a selected distance from the aperture of the optical fiber such that the blocking element blocks light so that the optical fiber does not collect light emitted from plasma in regions beyond the blocking element, wherein the light blocking element comprises an electrical probe element; and (d) a collimating channel formed in the support arm extending from the aperture of the optical fiber to an opening such that the optical fiber is spaced from the opening of the collimating channel, the collimating channel restricting the field of view of the aperture of the optical fiber to the extent of the light blocking element thereby to spatially restrict the off axis volume from which light is collected by the optical fiber.

2. The probe of claim 1 wherein the optical fiber extends through an interior bore in the support arm.

3. The probe of claim 1 wherein the electrical probe element mounted to the distal end of the support arm is comprised of two electrically conducting charge collection plates mounted on and separated by an electrically insulating spacer in back-to-back relation, and further including electrical wires extending from connection to the plates and carried on the support arm.

4. The probe of claim 3 wherein the electrical plate facing the optical fiber is spaced about 2.5 cm from the end of the longitudinally extending support arm section in which the optical fiber is mounted.

5. The probe of claim 3 wherein the electrical plates are circular disks of metal and the spacer is a ceramic insulator.

6. The probe of claim 5 wherein the disks are formed of tantalum.

7. The probe of claim 1 wherein the support arm has an elongated straight section defining an axial direction and a bend section extending from the straight section at the end of which the blocking element is mounted.

8. The probe of claim 7 wherein the bend section is U-shaped including a segment extending radially from the end of the elongated support arm section, then a segment extending axially, and then a segment extending radially inwardly at the end of which the blocking element is mounted.

9. A probe for plasma measurements comprising:

(a) a probe support arm with a distal end;

(b) an optical fiber carried by the support arm and having an aperture for the collection of light by the fiber; and (c) an electrical probe element mounted to the distal end of the support arm at a position spaced a selected distance from the aperture of the optical fiber such that the electrical probe element blocks light so that the optical fiber does not collect light emitted from plasma in regions beyond the electrical probe element, the electrical probe element comprised of two electrically conducting charge collection plates mounted on and separated by an electrically insulating spacer in back-to-back relation, and further including electrical wires extending from connection to the plates and carried on the support arm.

10. The probe of claim 9 wherein the support arm has an elongated straight section defining an axial direction and a bend section extending from the straight section at the end of which the electrical probe element is mounted such that the conducting plates are oriented perpendicular to the axial direction of the elongated support arm.

11. The probe of claim 10 wherein the bend section is U-shaped including a segment extending radially from the end of the elongated support arm section, then a segment extending axially, and then a segment extending radially inwardly at the end of which the spaced plates defining the electrical probe element are mounted.

12. The probe of claim 11 wherein the electrical plate facing the optical fiber is spaced about 2.5 cm from the end of the longitudinally extending support arm section in which the optical fiber is mounted.

13. The probe of claim 9 wherein the optical fiber extends through an interior bore in the support arm.

14. The probe of claim 9 including a collimating channel formed in the support arm extending from the aperture of the optical fiber to an opening such that the optical fiber is spaced from the opening of the collimating channel, the collimating channel restricting the field of view of the aperture of the optical fiber thereby to spatially restrict the off axis volume from which light is collected by the optical fiber.

15. The probe of claim 9 wherein the electrical plates are circular disks of metal and the spacer is a ceramic insulator.

16. The probe of claim 15 wherein the disks are formed of tantalum.

17. A method of measuring plasma characteristics with a probe, comprising the steps of:

(a) positioning a probe into a plasma;

(b) collecting light emitted in the plasma ar a light collection aperture carried by the probe;

(c) blocking light from entering the light collection aperture by a light blocking element comprising an electrical probe element carried by the probe at a position spaced a selected distance from the light collection aperture so that only light emitted by the plasma between the light blocking element and the aperture is collected by the aperture, and measuring the plasma with the electric probe element; and (d) collimating the light reaching the aperture by a channel carried by the probe to limit the field of view of the aperture to the light blocking element.

18. The method of claim 17 wherein the aperture is an end of an optical fiber and wherein the optical fiber further transmits the collected light to a remote location.

* * * * *